(12) United States Patent
Scaife et al.

(10) Patent No.: US 7,714,006 B1
(45) Date of Patent: *May 11, 2010

(54) METHODS OF MODIFYING THE BIOAVAILABILITY OF METAXALONE

(75) Inventors: Michael C. Scaife, Poway, CA (US); Charles C. Davis, San Diego, CA (US)

(73) Assignee: King Pharmaceuticals Research & Development, Inc., Cary, NC (US)

( * ) Notice: Subject to any disclaimer, the term of this patent is extended or adjusted under 35 U.S.C. 154(b) by 1138 days.

This patent is subject to a terminal disclaimer.

(21) Appl. No.: 11/182,661

(22) Filed: Jul. 15, 2005

Related U.S. Application Data

(63) Continuation of application No. 10/420,804, filed on Apr. 23, 2003, now abandoned, which is a continuation-in-part of application No. 10/386,113, filed on Mar. 12, 2003, now abandoned, which is a continuation of application No. 10/104,044, filed on Mar. 25, 2002, now Pat. No. 6,683,102, which is a continuation of application No. 09/998,206, filed on Dec. 3, 2001, now Pat. No. 6,407,128.

(51) Int. Cl.
*A61K 31/42* (2006.01)
(52) U.S. Cl. .................................... 514/376
(58) Field of Classification Search ................ 514/376
See application file for complete search history.

(56) References Cited

U.S. PATENT DOCUMENTS

| | | | |
|---|---|---|---|
| 3,062,827 A | 11/1962 | Lunsford | 260/307 |
| 3,993,767 A | 11/1976 | Alphin et al. | 424/272 |
| 4,036,957 A | 7/1977 | Alphin et al. | 424/232 |
| 4,058,621 A | 11/1977 | Hill | |
| 4,208,405 A | 6/1980 | Fouad | |
| 4,784,852 A | 11/1988 | Johansson | |
| 4,792,449 A | 12/1988 | Ausman et al. | 424/440 |
| 4,820,690 A | 4/1989 | Gregory et al. | 514/12 |
| 4,963,361 A | 10/1990 | Kawazi | 424/443 |
| 5,538,954 A | 7/1996 | Koch et al. | 514/53 |
| 5,785,976 A | 7/1998 | Westesen et al. | |
| 5,840,688 A | 11/1998 | Tso | 514/12 |
| 5,977,175 A | 11/1999 | Lin | 514/558 |
| 5,989,583 A | 11/1999 | Amselem | 424/439 |
| 6,017,932 A | 1/2000 | Singh et al. | 514/321 |
| 6,028,054 A | 2/2000 | Benet et al. | 514/9 |
| 6,030,988 A | 2/2000 | Gilis et al. | |
| 6,099,859 A | 8/2000 | Cheng et al. | 424/464 |
| 6,103,269 A | 8/2000 | Wunderlich et al. | |
| 6,114,379 A | 9/2000 | Wheelwright et al. | |
| 6,143,325 A | 11/2000 | Dennis et al. | 424/468 |
| 6,197,757 B1 | 3/2001 | Perrier et al. | |
| 6,207,178 B1 | 3/2001 | Westesen et al. | |
| 6,265,438 B1 | 7/2001 | Steward | |
| 6,683,102 B2 | 3/2002 | Scaife et al. | |
| 6,407,128 B1 | 6/2002 | Scaife et al. | 514/376 |
| 2001/0024659 A1 | 9/2001 | Chen et al. | 424/457 |
| 2002/0009474 A1 | 1/2002 | Adusumilli et al. | |

OTHER PUBLICATIONS

Clinical Study Report, ELN151607, Report date: Oct. 1, 2001.
Clinical Study Report, ELN151607-103, Report Date: Feb. 26, 2002.
U.S. Appl. No. 10/764,736, filed Jan. 26, 2004, Scaife et al.
U.S. Appl. No. 10/764,729, filed Jan. 26, 2004, Scaife et al.
U.S. Appl. No. 10/764,705, filed Jan. 26, 2004, Scaife et al.
U.S. Appl. No. 10/764,706, filed Jan. 26, 2004, Scaife et al.
U.S. Appl. No. 10/386,113, Scaife et al.
U.S. Appl. No. 10/420,804, Scaife et al.
U.S. Appl. No. 10/764,798, Scaife et al.
Elan Pharmaceuticals, Inc., Skelaxin (metaxalone) tablets NDA 13-217/S-047 Labeling Supplement, vols. 1 and 2, Apr. 21, 2003.
Lunsford et al., 5-Aryloxymethyl-2-oxazolidinones, J. of Am. Chemical Soc., vol. 82, No. 5 Mar. 1960, pp. 1166-1171.
Physicians' Desk Reference, Med. Economics Co. Inc., Montvale NJ, 55th Edition, 2001 p. 1080.
The Merck Index, 11th edition, (Budavari et al Eds.) Merck & Co. Inc., Rahway NJ 1989, pp. 933-934.
"Skeletal Muscle Relaxants (Systemic)," Micromedex, Inc., reported to have been revised Aug. 11, 1995, printed from http://www.nlm.nih.gov/medilineplus/druginfo/uspdi/202523.html on Sep. 13, 2002, pp. 1-7.
Kazem Fathie, "Musculoskeletal Disorders and Their Management with a New Relaxant," printed from http://www.aanos.org/edctn_msk_disordr.htm (the website of the American Academy of Neurological and Orthopaedic Surgeons) on Sep. 13, 2002, pp. 1-5.
Kazem Fathie, "Musculoskeletal Disorders and Their Management with a New Relaxant," Clinical Medicine, Apr. 1965, pp. 678-682.
Kazem Fathie, A second look at a skeletal muscle relaxant: a double-blind study of metaxlone Current Therapeutic Research, vol. 6, No. 11, 1964.
Morey et al., Metaxalone, A New Skeletal Muscle Relaxant Journal A.O.A. vol. 62, pp. 517-521 (1963).
Elenbaas, "Centrally Acting Oral Skeletal Muscle Relaxants," Am.J. Hosp.Pharm. vol. 37, pp. 1313-1323 (1980).
Physicians' Desk Reference, Med. Economics Co. Inc., Oradell NJ, 41st Edition, 1987, p. 827.
Clinical Study Report, ELN151607-105; report date: Apr. 16, 2003.
Abrams et al., *Skeletal Muscle Relaxants*, in Clinical Drug Therapy: Rationales for Nursing Practice 145-49 (J.B. Lippincott Co. 4th ed. 1995).
Albanese, *Metaxalone*, in Nurses' Drug Reference 427 (McGraw-Hill Book Co. 2d ed. 1982).
Dent et al., *A Study of Metaxalone (Skelaxin) Vs. Placebo in Acute Musculoskeletal Disorders: A Cooperative Study*, Curr. Therapeutic Res., 18(3), 433-40 (1975).
Memorandum and Order issued in *King Pharm., Inc. v. Eon Labs, Inc.*, No. 04-cv-5540 (E.D.N.Y. Jan. 20, 2009), reported at 593 F. Supp. 2d 501.
Brief for Plaintiffs-Appellants filed in *King Pharm., Inc. v. Eon Labs, Inc*, Nos. 2009-1437 & -1438 (Fed. Cir. Nov. 23, 2009).

*Primary Examiner*—Raymond J Henley, III
(74) *Attorney, Agent, or Firm*—Jones Day

(57) ABSTRACT

A method of increasing the bioavailability, and decreasing the effect of age on the bioavailability, of metaxalone, by administration of an oral dosage form with food is provided, as well as an article of manufacture comprising an oral dosage form of metaxalone in a suitable container and associated with printed labeling which describes the increased bioavailability, and decreased effect of age on bioavailability, of the medication in the container, when taken with food.

27 Claims, 1 Drawing Sheet

METHODS OF MODIFYING THE BIOAVAILABILITY OF METAXALONE

CROSS-REFERENCE TO RELATED APPLICATIONS

This application is a continuation of U.S. application Ser. No. 10/420,804, filed Apr. 23, 2003, now abandoned, which is a continuation-in-part application of U.S. application Ser. No. 10/386,113, filed Mar. 12, 2003, now abandoned, which is a continuation of U.S. application Ser. No. 10/104,044, filed Mar. 25, 2002, which issued Jan. 27, 2004 as U.S. Pat. No. 6,683,102, which is a continuation of U.S. application Ser. No. 09/998,206, filed Dec. 3, 2001, which issued Jun. 18, 2002 as U.S. Pat. No. 6,407,128, all of which are hereby incorporated by reference in their entirety.

FIELD OF THE INVENTION

The invention relates to methods for controlling the bioavailability of a medicinal agent, namely metaxalone (5-[(3,5-dimethylphenoxy)methyl]-2 oxazolidinone).

BACKGROUND OF THE INVENTION

Metaxalone (Skelaxin®) has the following chemical structure and name:

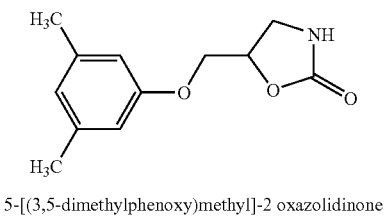

5-[(3,5-dimethylphenoxy)methyl]-2 oxazolidinone

Skelaxin is indicated as an adjunct to rest, physical therapy, and other measures for the relief of discomforts associated with acute, painful musculoskeletal conditions. The mode of action of this drug has not been clearly identified, but may be related to its sedative properties. Metaxalone does not directly relax tense skeletal muscles in man. The commercially available tablet contains: metaxalone, 400 mg along with inert compression tableting excipients.

Metaxalone is further described at Monograph no. 5838 of the Merck Index (Eleventh Addition, Merck & Co., 1989) and is also identified by CAS Registry Number: 1665-48-1. It is also known by the drug code, AHR-438, and the drug product containing metaxalone is marketed as Skelaxin® (a trademark of Elan Pharmaceuticals, Inc.).

Preparation of metaxalone is described in Lunsford et al., J. Am. Chem. Soc. 82, 1166 (1960) and U.S. Pat. No. 3,062,827 to Lunsford (Nov. 6, 1962, Assignee A. H. Robins), which is incorporated herein in its entirety by reference. The '827 patent discloses the compound and related species as anticonvulsants and antispasmodics; however, these activities have not been borne out by clinical experience.

Metaxalone is a central nervous system depressant that has sedative and skeletal muscle relaxant effects. Metaxalone is indicated as an adjunct to rest, physical therapy and other measures for the relief of discomforts associated with acute, painful musculoskeletal conditions. See Skelaxin® monograph, 2001 Physicians' Desk Reference®, Medical Economics Company, Inc. (publisher) Montvale, N.J.

The most frequent reactions to metaxalone include nausea, vomiting, gastrointestinal upset, drowsiness, dizziness, headache, and nervousness or "irritability." Other adverse reactions include hypersensitivity reaction, characterized by a light rash with or without pruritus; leukopenia; hemolytic anemia; and jaundice.

Pharmacokinetic studies have not previously been conducted to date to evaluate the effect of food on the pharmacokinetics of metaxalone. The hydrophobicity of the metaxalone molecule and the dosage amount required for a therapeutic effect both point to probably limited absorption from the gut when administered orally. More oral bioavailability of the drug substance has been sought to increase both speed of onset and amount of therapeutic effect.

SUMMARY OF THE INVENTION

Figure 1:
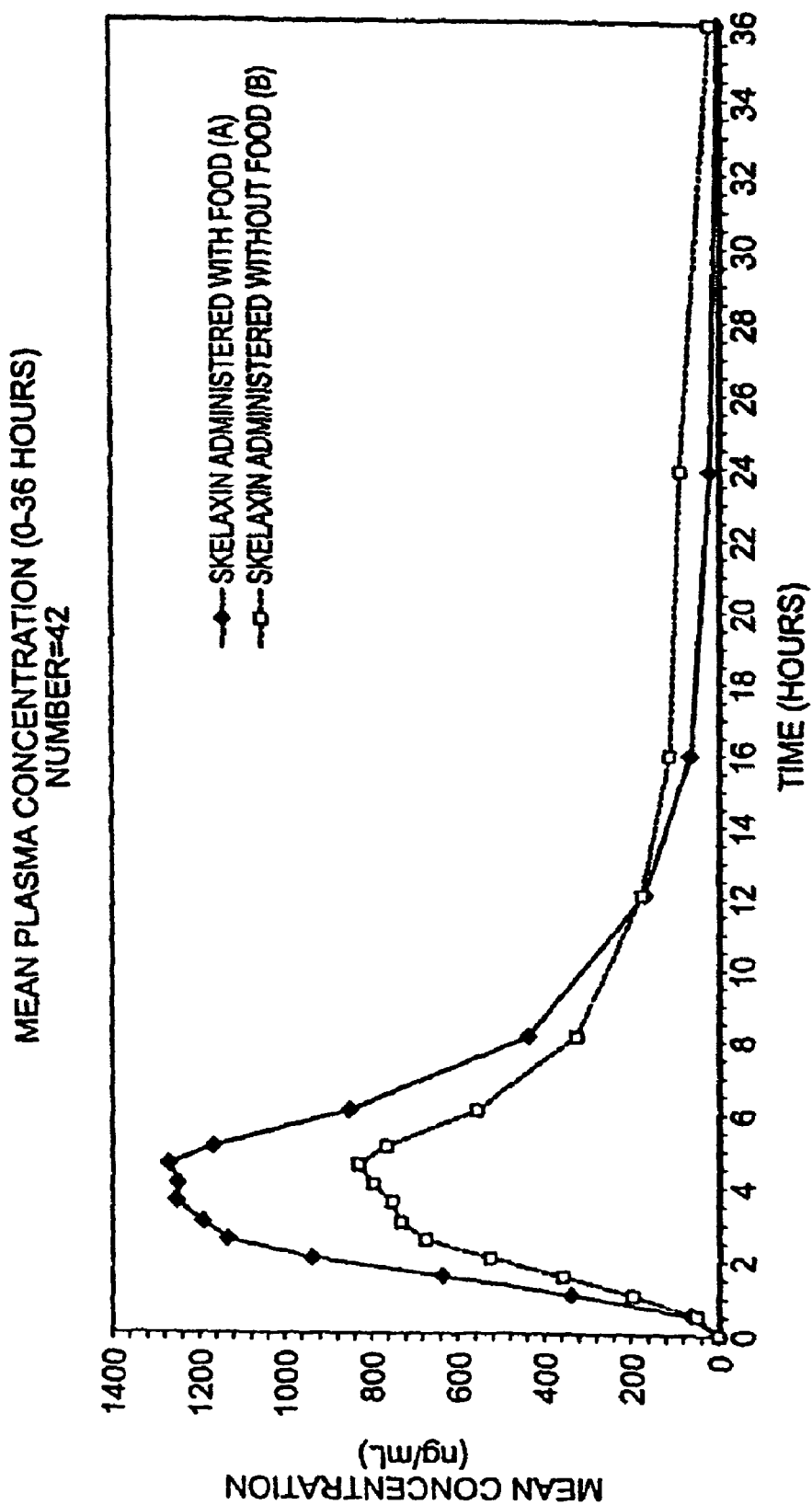
FIG. 1 is a plot of the mean plasma concentration of metaxalone ht nanograms per milliliter versus the time elapsed from administration of the dosage form. Two (2) plots are shown for the 400 mg dosage form administered with and without food.

The subject of this invention is the unexpected finding that administration of metaxalone with food increases both the rate and extent of absorption via the oral dosage form in human subjects.

One aspect of this invention is a method of increasing the bioavailability of metaxalone in a human patient receiving metaxalone therapy wherein the metaxalone is contained in a pharmaceutical composition, which method comprises administering a therapeutically effective amount of metaxalone to the patient with food.

Another aspect of the invention is providing a method of increasing rate and extent of metaxalone absorption as measured by the drug concentration attained in the blood stream over time of a patient receiving the drug in an oral dosage form, which method comprises administering a therapeutically effective amount of metaxalone to the patient with food.

Another aspect of the invention includes a method to better standardize the bioavailability by administering the drug with food. This aspect is especially applicable to decreasing the effect of age on bioavailability. Stated another way, this aspect of the invention allows for a reduction in the age-related variability in bioavailability.

Preferably the therapeutic amount is between about 200 mg to about 900 mg, and more preferably between about 400 mg to about 800 mg. Unit dosage forms are preferred.

Preferably the food is a solid food with sufficient bulk and fat content that it is not rapidly dissolved and absorbed in the stomach. More preferably the food is a meal, such as breakfast, lunch, or dinner. Advantageously the dosage is administered to the patient between about 30 minutes prior to about 2 hours after eating a meal, most advantageously the dosage is administered within 15 minutes of eating a meal. The terms "without food," "fasted," and "an empty stomach" are defined to mean the condition of not having consumed solid food for about 1 hour prior to until about 2 hours after such consumption.

Yet another aspect of this invention is providing information to prescribing physicians and patients receiving metaxalone therapy useful in maximizing the therapeutic effect of the oral dosage form, by recommending that metaxalone be taken within about half an hour of consuming food. This advice is useful for improving bioavailability and reducing the effect of age on bioavailability.

Another aspect of this invention is an article of manufacture that comprises a container containing a pharmaceutical composition comprising metaxalone wherein the container holds preferably the metaxalone composition in unit dosage form and is associated with printed labeling instructions advising of the differing absorption when the pharmaceutical composition is taken with and without food.

Analysis #1: Food Effect (1×400 mg Tablet)

The effect of food on metaxalone absorption was identified in a study designed to compare the bioavailability of 400 mg of metaxalone in the formulation the drug product Skelaxin® administered to healthy volunteers with and without food.

An objective was to evaluate the bioavailability of metaxalone when administered to subjects with and without food. A single center, single dose, open-label, two-period, randomized, crossover trial in healthy subjects was conducted over a period of approximately 32 days.

The two study drug treatments were as follows:

Treatment A: metaxalone tablet (400 mg) administered with food

Treatment B: metaxalone tablet (400 mg) administered without food

In fed treatment condition A, study drug was taken 15 minutes after the test meal. The test meal was consumed over a 15 minute time period. There was a 6-day washout period between study drug administrations. Seventeen blood samples were collected, starting with baseline (0 hour) and at the following time points: 0.5, 1, 1.5, 2, 2.5, 3, 3.5, 4, 4.5, 5, 6, 8, 12, 16; 24, and 36 hours.

A total of 44 subjects (31 males/13 females) were enrolled and dosed. Only the plasma of subjects who completed the study were assayed and used for the pharmacokinetic analysis.

A single center, single dose, open label, two-period crossover trial was devised for study in healthy subjects. Each administration was a single oral dose of one Skelaxin® 400 mg tablet with or without food. The study drug was administered as follows:

Treatment A: One (1) 400 mg tablet of metaxalone with 240 mL of room temperature water with food: Breakfast was given to the subjects 30 Minutes prior to dosing and eaten within a 15 minute period. The dose of study drug was administered to the subjects 15 minutes after the breakfast was finished.

The breakfast consisted of the following:

2 eggs (fried in butter);

2 strips of bacon;

2 slices of toast with butter;

4 ounces of hash brown potatoes; and 1 glass whole milk (8 ounces).

Treatment B: One (1) 400 mg tablet of metaxalone with 240 mL of room temperature water without food. The study drug was administered with 240 mL room temperature water. A mouth check was performed to verify that the subjects swallowed the dose. Subjects were sequentially dosed at 1-minute intervals. The actual time of dosing was recorded on the Master Flow Sheet (refer to the Appendix 16.3.2 Clinical Study Data). Drug administration (1×400 mg tablet) was assisted with 240 mL of room temperature water consumed under direct observation. Immediately after administration of product, the subject's oral cavity was checked to confirm complete medication and fluid consumption. Dosing was completed as scheduled in 42 of 44 subjects.

The drug substance, metaxalone, was dosed in tablet form. Content 400 mg; Route: Oral, Batch/Lot No.: SKLWW263F; Expiration Date: FEB03; Manufacturer: West-Ward Pharmaceutical Corp.

All pharmacokinetic parameters were analyzed by non-compartmental methods. The following PK parameters were calculated for the two PK profiles and are defined as follows:

$T_{max}$: Time to maximum concentration;

$C_{max}$: Observed maximum concentration;

kel: Slope of terminal linear portion of concentration/time curve;

T1/2: Half-life of metaxalone calculated as: 0.693/Kel;

AUC(last): Area under the curve to last quantifiable concentration as measured by the trapezoidal rule;

AUC(inf): The AUC value extrapolated to infinity calculated as:

AUC(inf)=AUC(last)+C(t)last/Kel where C(t)last is the last measurable concentration.

Statistical Analysis

All statistical analyses were performed using SAS® software version 6.08 or higher. The pharmacokinetic parameters between the two treatments were compared using an appropriate ANOVA model (analysis of variance) that includes terms for treatment, sequence, and period effect. Ninety percent confidence intervals were computed for the Cmax and AUC values of the fed treatment with fasting as the reference treatment. During the study there were no protocol deviations to confound the pharmacokinetic and bioavailability analyses. Study results were not corrected for drug potency. The individual test results are summarized in TABLE I:

TABLE I

Summary of AUC(inf) and Ln-Transformed AUC(inf) for Skelaxin ® Administered With Food (A) vs. Skelaxin ® Administered Without Food (B)

| Subj | Seq. | A: With Food (ng/mL) | B: Without Food (ng/mL) | (A − B) | Ratio (A/B) | % Ratio (A/B) * 100 | $Log_e$ A Ln(A) | $Log_e$ B Ln(B) | $Log_e$ Ratio Ln (Ratio) |
|---|---|---|---|---|---|---|---|---|---|
| 2 | 1 | 9031 | 9855 | 824 | 0.916 | 91.64 | 9.108 | 9.196 | 0.087 |
| 3 | 2 | 9609 | 13103 | 3494 | 0.733 | 73.33 | 9.170 | 9.481 | 0.310 |
| 4 | 2 | 5011 | 3867 | 1144 | 1.296 | 129.58 | 8.519 | 8.260 | 0.259 |
| 5 | 1 | 3389 | 2530 | 859 | 1.340 | 133.95 | 8.128 | 7.836 | 0.292 |
| 6 | 2 | 10456 | 7302 | 3154 | 1.432 | 143.19 | 9.255 | 8.896 | 0.359 |
| 7 | 2 | 11217 | 11103 | 114 | 1.010 | 101.03 | 9.325 | 9.315 | 0.010 |

TABLE I-continued

Summary of AUC(inf) and Ln-Transformed AUC(inf) for
Skelaxin ® Administered With Food (A) vs. Skelaxin ® Administered Without Food (B)

| Subj | Seq. | A: With Food (ng/mL) | B: Without Food (ng/mL) | (A − B) | Ratio (A/B) | % Ratio (A/B) * 100 | $Log_e$ A Ln(A) | $Log_e$ B Ln(B) | $Log_e$ Ratio Ln (Ratio) |
|---|---|---|---|---|---|---|---|---|---|
| 8  | 2 | 4025  | 3857  | 168  | 1.044 | 104.36 | 8.300 | 8.258 | 0.043 |
| 9  | 2 | 13708 | 8876  | 4832 | 1.544 | 154.44 | 9.526 | 9.091 | 0.435 |
| 11 | 2 | 8122  | 6570  | 1552 | 1.236 | 123.62 | 9.002 | 8.790 | 0.212 |
| 12 | 1 | 6739  | 5470  | 1269 | 1.232 | 123.20 | 8.816 | 8.607 | 0.209 |
| 13 | 2 | 4614  | 4360  | 254  | 1.058 | 105.83 | 8.437 | 8.380 | 0.057 |
| 14 | 1 | 17347 | 13467 | 3880 | 1.288 | 128.81 | 9.761 | 9.508 | 0.253 |
| 15 | 2 | 5488  | 3535  | 1953 | 1.552 | 155.25 | 8.610 | 8.170 | 0.440 |
| 16 | 1 | 12327 | 12025 | 302  | 1.025 | 102.51 | 9.420 | 9.395 | 0.025 |
| 17 | 1 | 4070  | 3320  | 750  | 1.226 | 122.59 | 8.311 | 8.108 | 0.204 |
| 18 | 1 | 5296  | 4365  | 931  | 1.213 | 121.33 | 8.575 | 8.381 | 0.193 |
| 19 | 2 | 8022  | 8271  | 249  | 0.970 | 96.99  | 8.990 | 9.021 | 0.031 |
| 20 | 2 | 2962  | 2874  | 88   | 1.031 | 103.06 | 7.994 | 7.963 | 0.030 |
| 21 | 1 | 9143  | 7173  | 1970 | 1.275 | 127.46 | 9.121 | 8.878 | 0.243 |
| 22 | 2 | 11873 | 7742  | 4131 | 1.534 | 153.36 | 9.382 | 8.954 | 0.428 |
| 23 | 1 | 10456 | 9983  | 473  | 1.047 | 104.74 | 9.255 | 9.209 | 0.046 |
| 24 | 1 | 6507  | 5529  | 978  | 1.177 | 117.69 | 8.781 | 8.618 | 0.163 |
| 25 | 2 | 12143 | 10272 | 1871 | 1.182 | 118.21 | 9.405 | 9.237 | 0.167 |
| 26 | 1 | 4519  | 5391  | 872  | 0.838 | 83.82  | 8.416 | 8.592 | 0.176 |
| 27 | 1 | 5208  | 5061  | 147  | 1.029 | 102.90 | 8.558 | 8.529 | 0.029 |
| 28 | 2 | 5197  | 5012  | 185  | 1.037 | 103.69 | 8.556 | 8.520 | 0.036 |
| 29 | 1 | 10355 | 11601 | 1246 | 0.893 | 89.26  | 9.245 | 9.359 | 0.114 |
| 30 | 1 | 7350  | 6452  | 898  | 1.139 | 113.92 | 8.902 | 8.772 | 0.130 |
| 31 | 1 | 7899  | 7677  | 222  | 1.029 | 102.89 | 8.974 | 8.946 | 0.029 |
| 32 | 2 | 6719  | 4440  | 2279 | 1.513 | 151.33 | 8.813 | 8.398 | 0.414 |
| 33 | 2 | 11295 | 11316 | 21   | 0.998 | 99.81  | 9.332 | 9.334 | 0.002 |
| 34 | 2 | 13357 | 13580 | 223  | 0.984 | 98.36  | 9.500 | 9.516 | 0.017 |
| 35 | 2 | 10710 | 10138 | 572  | 1.056 | 105.64 | 9.279 | 9.224 | 0.055 |
| 36 | 1 | 19077 | 19329 | 252  | 0.987 | 98.70  | 9.856 | 9.869 | 0.013 |
| 37 | 1 | 6727  | 4454  | 2273 | 1.510 | 151.03 | 8.814 | 8.402 | 0.412 |
| 38 | 2 | 19024 | 9934  | 9090 | 1.915 | 191.50 | 9.853 | 9.204 | 0.650 |
| 39 | 1 | 3060  | 3284  | 224  | 0.932 | 93.18  | 8.026 | 8.097 | 0.071 |
| 40 | 1 | 5188  | 4203  | 985  | 1.234 | 123.44 | 8.554 | 8.344 | 0.211 |
| 41 | 1 | 7273  | 6574  | 699  | 1.106 | 110.63 | 8.892 | 8.791 | 0.101 |
| 42 | 2 | 3958  | 3642  | 316  | 1.087 | 108.68 | 8.283 | 8.200 | 0.083 |
| 43 | 1 | 8837  | 4642  | 4195 | 1.904 | 190.37 | 9.087 | 8.443 | 0.644 |
| 44 | 2 | 11427 | 11935 | 508  | 0.957 | 95.74  | 9.344 | 9.387 | 0.043 |

Differences were declared to be significant at the 5% level. The ratio of the geometric means for the ln-transformed data and the corresponding 90% confidence intervals were calculated for AUC(last), AUC(inf), and Cmax. The calculations for the confidence intervals used the least squares means (LSMEANS) and the standard errors of the estimate, both generated by the SAS® software.

The lower limit of quantitation for metaxalone was 10 ng/mL. For statistical analysis, subject sample values below the lower limit of quantitation were reported as zero.

Tables IIa and IIb summarize the results of the analyses performed on the pharmacokinetic parameters obtained from the fed and fasted states.

TABLE IIa

| Metaxalone | Ln-Transformed AUC(last) | Ln-Transformed AUC(inf) | Ln-Transformed Cmax |
|---|---|---|---|
| Treatment A Geometric Mean | 7525.00 | 7630.53 | 1536.23 |
| Treatment B Geometric Mean | 6094.12 | 6615.24 | 865.34 |
| % Ratio | 123.48 | 115.35 | 177.53 |
| 90% Confidence Interval | (116.40, 130.99) | (109.24, 121.80) | (156.62, 201.23) |

TABLE IIb

| Metaxalone | AUC(last) | AUC(inf) | Cmax | Tmax | $T_{1/2}$ |
|---|---|---|---|---|---|
| Treatment A Least Squares Mean | 8439.62 | 8541.31 | 1773.61 | 4.29 | 2.37 |
| Treatment B Least Squares Mean | 6961.81 | 7478.90 | 983.37 | 3.32 | 9.04 |

At the 5% significance level, the ANOVA detected statistically significant differences between treatments for ln-transformed AUC(last), AUC(inf), and Cmax, as well as for untransformed AUC(last), AUC(inf), Cmax, Tmax, T1/2; and Kel. The ANOVA detected no statistically significant differences between periods or between sequences.

The mean $T_{1/2}$ (half-life) of metaxalone with food and without food were 2.37 and 9.04 hours respectively. The exact reason for this discrepancy is unclear. However, the AUC (last) is outside the confidence interval, indicating a significant food effect.

Ratio (A/B) of least-squares means for AUC(last), AUC (inf) and Cmax were 123.48%, 115.35% and 177.53%, respectively demonstrating that metaxalone administered with food increased both its rate and extent of absorption.

ANOVA detected statistically significant differences between treatments for ln-transformed AUC(last), AUC(inf), and Cmax, as well as for untransformed AUC(last), AUC(inf), Cmax, $T_{1/2}$, and Kel. ANOVA did not detect any statistically significant differences between treatments for untransformed Tmax.

Conclusion from Analysis #1: Administration with food increases both the rate and extent of absorption of metaxalone 400 mg tablets when administered as a single dose. The bioavailability of metaxalone 400 mg tablets increased when administrated with food.

Analysis #2; Effects of Age and Gender on Metaxalone Pharmacokinetic Parameters Under Fed and Fasted Conditions 1. Introduction This analysis considers the effects of age and gender on three pharmacokinetic (PK) parameters of metaxalone under fed and fasted conditions. The three parameters are:

Cmax: the observed maximum plasma concentration (ng/mL);

AUC(last): the area under the curve (AUC) to the last quantifiable concentration, as measured by the trapezoidal rule (ng-hr/mL);

AUC(inf): the AUC extrapolated to infinity (ng-hr/mL).

Because the distributions of these parameters tend to be skewed, and in accordance with generally accepted practice, all analyses are carried out after computing the natural logarithm (ln) of the values of the PK parameters from individual subjects.

The report is based primarily on two similarly designed studies in which PK parameters were determined under fed and fasted conditions for the 2×400 mg dose of metaxalone:

Study AN151607-103 (hereafter referred to as the 103 study): a four-period, randomized crossover trial with treatment conditions 2×400 mg with food, 2×400 mg without food, 1×800 mg with food, 1×800 mg without food; and Study ELN151607-105 (hereafter referred to as the 105 study): a two-period, randomized crossover trial with treatment conditions 2×400 mg with food and 2×400 mg without food.

In addition, the robustness of the results are assessed by applying similar analysis approaches to the data from two other studies:

Study AN151607-101 (hereafter referred to as the 101 study): a two-period, randomized crossover trial with treatment conditions 1×400 mg with food and 1×400 mg without food;

Study AN151607-106 (hereafter referred to as the 106 study): a single dose trial with treatment condition 2×400 mg without food.

The report is organized as follows: Section 2 presents the methods and results of analyses of the effect of age on the fed and fasted values of the PK parameters. Section 3 extends the results of Section 2 by examining the joint effects of age and gender. Finally, Section 4 summarizes the conclusions.

Section 2. Effects of Age on Cmax, AUC(last), and AUC (inf)

2.1 Introduction

Using the 2×400 mg data from studies 103 and 105, Section 2.2 presents the results of analyses of the effects of age on the fed values of Cmax, AUC(last), and AUC(inf). Section 2.3 similarly reports the results of analyses of fasted values of these parameters using the 2×400 mg data from these two studies. Section 2.4 repeats the analyses of Sections 2.2 and 2.3 using the data from the 1×800 mg treatment of study 103, in combination with the 2×400 mg data from study 105. Finally, Sections 2.5 and 2.6 report the results of similar analyses using the data from studies 101 and 106, respectively.

The primary results are based on the results of linear regression models investigating the effects of age on each PK parameter. Descriptive analyses reporting parametric (Pearson) and nonparametric (Spearman) correlation coefficients between age and each PK parameter are also provided. The Pearson correlation coefficient measures the extent of the linear association between two variables and is most appropriate when the data are approximately bivariate normally distributed with no outliers. The Spearman correlation coefficient is based on the ranks of the variables. It is less sensitive to outliers, but is often also a less sensitive measure of the strength of association.

2.2 Effects of Age on Fed Values of PK Parameters Using the 2×400 mg Data from Studies 103 and 105

In study 103, 59 subjects were administered the 2×400 mg dose under fed conditions. The mean age was 26.1 years, with a range from 18 to 50 years. (A total of 64 subjects began the study, of which the average age was 25.6 years. Five subjects were not included in the pharmacokinetic analysis.) In study 105, 44 subjects were administered the 2×400 mg dose under fed conditions. The mean age in study 105 was 56.0 years; with a range from 18 to 81 years.

First, in the combined group of 59+44=103 subjects, Pearson and Spearman correlation coefficients between age and each of the three PK parameters were computed. The correlation coefficients and two-sided p-values from the test of the null hypothesis of no association are shown below in TABLE IIIa:

TABLE IIIa

| | | ln(Cmax) | ln(AUC(last)) | ln(AUC(inf)) |
|---|---|---|---|---|
| Pearson | correlation | 0.007 | 0.197 | 0.207 |
| | p-value | 0.942 | 0.046 | 0.036 |
| Spearman | correlation | 0.042 | 0.230 | 0.236 |
| | p-value | 0.674 | 0.019 | 0.016 |

For ln(Cmax), there is essentially no association with age. For ln(AUC(last)) and ln(AUC(inf)), there is a modest positive association (correlation coefficients approximately equal to 0.2) that is statistically significantly different from zero.

Linear regression models using the natural logarithm of each of the three PK parameters as the dependent variable and age as the independent variable were fitted in order to estimate the magnitude of the associations with age. The estimated age effects are displayed below in TABLE IIIb, as well as the value of $R^2$ (proportion of variability explained by age) from each model.

TABLE IIIb

|  | ln(Cmax) | ln(AUC(last)) | ln(AUC(inf)) |
|---|---|---|---|
| Regression coefficient of age | 0.0002 | 0.0044 | 0.0045 |
| $R^2$ | 0.0001 | 0.039 | 0.043 |

The expected value of ln(Cmax) is estimated to increase by 0.0002 for each one-year increase in age. Similarly, the effects of a one-year increase in age on ln(AUC(last)) and ln(AUC(inf)) are estimated to be 0.0044 and 0.0045, respectively. Only 0.01% of the variability in ln(Cmax) is explained by age, while only about 4% of the variability in ln(AUC(last)) and ln(AUC(inf)) is explained by age. As an aid in interpreting the magnitudes of the effects of age, the expected value of ln(Cmax) is 0.1% higher for a 70-year-old individual than for a 20-year-old individual, while the expected values of ln(AUC(last)) and ln(AUC(inf)) are approximately 2% higher for a 70-year-old individual than for a 20-year-old individual. On the untransformed scale, the percentage increases are much larger for the two AUC parameters (24% and 25%, respectively), but the percentage increase in Cmax for a 70-year-old individual as compared to a 20-year-old individual is still only 0.1%.

2.3 Effects of Age on Fasted Values of PK Parameters Using the 2×400 mg Data from Studies 103 and 105

In study 103, the same 59 subjects were administered the 2×400 mg dose under fasted conditions. Similarly, the 44 subjects from study 105 were administered the 2×400 mg dose under fasted conditions.

First, in the combined group of n=103 subjects, Pearson and Spearman correlations between age and each of the three PK parameters were computed. The correlation coefficients and two-sided p-values from the test of the null hypothesis of no association are shown below in TABLE IVa:

TABLE IVa

|  |  | ln(Cmax) | ln(AUC(last)) | ln(AUC(inf)) |
|---|---|---|---|---|
| Pearson | correlation | 0.531 | 0.514 | 0.510 |
|  | p-value | <0.001 | <0.001 | <0.001 |
| Spearman | correlation | 0.545 | 0.533 | 0.533 |
|  | p-value | <0.001 | <0.001 | <0.001 |

For all three PK parameters, the correlations are much larger than they were under fed conditions. AU correlations are highly statistically significantly different from zero.

Linear regression models using the natural logarithm of each of the three PK parameters as the dependent variable and age as the independent variable were fitted in order to estimate the magnitude of the associations with age. The estimated age effects and values of $R^2$ are displayed below in TABLE IVb.

TABLE IVb

|  | ln(Cmax) | ln(AUC(last)) | ln(AUC(inf)) |
|---|---|---|---|
| Regression coefficient of age | 0.0142 | 0.0137 | 0.0133 |
| $R^2$ | 0.282 | 0.264 | 0.260 |

A one-year increase in age gives an estimated increase of 0.0142 for ln(Cmax), 0.0137 for ln(AUC(last)), and 0.0133 for ln(AUC(inf)). For ln(AUC(last)) and ln(AUC(inf)), the estimated regression coefficients for age are approximately three times larger under fasted conditions than under fed conditions. The increase is even more striking for ln(Cmax), where the estimated effect of age under fasted conditions is more than 70 times as large as the corresponding estimated effect under fed conditions. The values of $R^2$ indicate that more than 25% of the variability of these parameters in the fasted condition is explained by age. This reflects the fact that age is much more strongly associated with the PK parameters in the fasted condition than in the fed condition.

As in Section 2.2, the magnitudes of the estimated effects of age under fasted conditions can be more easily illustrated by considering the percentage increases when comparing a 70-year-old individual to a 20-year-old individual. On the natural log scale, these increases are 10%, 7%, and 7% for ln(Cmax), ln(AUC(last)), and ln(AUC(inf)), respectively. These increases are much larger than the corresponding percentage changes in the fed condition (Section 2.2). The differences are even greater on the untransformed scale: 103% for Cmax, 98% for ln(AUC(last)), and 95% for ln(AUC(inf)). These percentage differences for the AUC parameters are approximately four times as large as the corresponding percentage differences in the fed condition (Section 2.2). The difference between fed and fasted is even greater for Cmax (a 103% increase for fasted, compared with a 0.1% increase for fed).

2.4 Effects of Age on Fed and Fasted Values of PK Parameters Using the 1×800 ma Data from Study 103 and the 2×400 mg Data from Study 105

It is possible to somewhat independently assess the consistency of these results by repeating the analyses of Sections 2.2 and 2.3 using the 1×800 fed and fasted results from study 103. These analyses are still based on the combined group of n=103 subjects (59 from study 103, 44 from study 105). However, the fed and fasted PK values from the 1×800 dosage of study 103 are used instead of the data from the 2×400 dosage.

The correlation coefficients under fed and fasted conditions are displayed below in TABLE Va:

TABLE Va

|  |  | ln(Cmax) | ln(AUC(last)) | ln(AUC(inf)) |
|---|---|---|---|---|
|  |  | Fed: |  |  |
| Pearson | correlation | 0.040 | 0.229 | 0.237 |
|  | p-value | 0.691 | 0.020 | 0.016 |
| Spearman | correlation | 0.086 | 0.276 | 0.281 |
|  | p-value | 0.388 | 0.005 | 0.004 |
|  |  | Fasted: |  |  |
| Pearson | correlation | 0.600 | 0.522 | 0.513 |
|  | p-value | <0.001 | <0.001 | <0.001 |
| Spearman | correlation | 0.635 | 0.522 | 0.514 |
|  | p-value | <0.001 | <0.001 | <0.001 |

Although the magnitudes of the correlation coefficients are generally somewhat larger than when using the 2×400 data from study 103, the overall patterns of the results are the same, as are the results of tests of statistical significance.

Similarly, the results of the linear regression models for the fed and fasted data are shown below in TABLE Vb:

TABLE Vb

|  | ln(Cmax) | ln(AUC(last)) | ln(AUC(inf)) |
|---|---|---|---|
| Fed: | | | |
| Regression coefficient of age | 0.0011 | 0.0051 | 0.0053 |
| $R^2$ | 0.0016 | 0.0523 | 0.0563 |
| Fasted: | | | |
| Regression coefficient of age | 0.0189 | 0.0147 | 0.0143 |
| $R^2$ | 0.3598 | 0.2724 | 0.2635 |

The estimated regression coefficients are similar to those from Sections 2.2 and 2.3. In addition, while approximately 5% or less of the variability of the fed PK parameters is explained by age, more than 25% of the variability of the fasted parameters is explained by age.

Thus, while not a totally independent confirmation (due to the fact that the 105 data are used in both analyses), these results indicate that the findings are relatively robust and that the effects seen with the 2×400 mg treatment are reproduced with the 1×800 mg treatment.

2.5 Effects of Age on Fed and Fasted Values of PK Parameters Using the Data from Study 101

2.5.1 Introduction

Study 101 was a two-period randomized crossover trial conducted in 42 healthy volunteers. The mean age was 23.8 years, with a range from 18 to 42 years. The treatment conditions were 1×400 mg with food and 1×400 mg without food. Because the treatments were not the same as in the 103 and 105 studies (1×400 mg in study 101, as opposed to 2×400 mg in studies 103 and 105), and additionally because the blood sample collection schedules were not the same, it is not possible to combine the 101 data with the data from studies 103 and 105. However, it is possible to independently investigate the effects of age on fed and fasted values of the PK parameters in order to determine if the effects are of similar magnitude and direction to those found in the 103 and 105 studies.

2.5.2 Effects of Age on Fed Values of Cmax, AUC(last), and AUC(inf)

First, Pearson and Spearman correlation coefficients between age and each of the three PK parameters were computed. The correlation coefficients and two-sided p-values from the test of the null hypothesis of no association are shown below in TABLE VIa:

TABLE VIa

|  |  | ln(Cmax) | ln(AUC(last)) | ln(AUC(inf)) |
|---|---|---|---|---|
| Pearson | correlation | 0.102 | 0.179 | 0.186 |
|  | p-value | 0.520 | 0.256 | 0.238 |
| Spearman | correlation | −0.009 | 0.022 | 0.029 |
|  | p-value | 0.953 | 0.888 | 0.854 |

For ln(Cmax), there is no noticeable association with age. While the Pearson correlation coefficient is positive, the Spearman correlation (which is based on the ranks of the observations) is slightly less than zero. For ln(AUC(last)) and ln(AUC(inf)), there is a modest positive association based on the Pearson correlation coefficient, but the Spearman correlation coefficients are much smaller and not much larger than zero. None of the correlation coefficients are statistically significantly different from zero.

Linear regression models using the natural logarithm of each of the three PK parameters as the dependent variable and age as the independent variable were fitted in order to estimate the magnitude of the associations with age. The estimated age effects, as well as the values of $R^2$, are displayed below in TABLE VIb.

TABLE VIb

|  | ln(Cmax) | ln(AUC(last)) | ln(AUC(inf)) |
|---|---|---|---|
| Regression coefficient of age | 0.0103 | 0.0154 | 0.0159 |
| $R^2$ | 0.0104 | 0.0321 | 0.0347 |

The estimated regression coefficients are small and not significantly different from zero. In addition, the proportion of variability explained by age is small (1% for ln(Cmax) and 3% for each of the two AUC parameters).

2.5.3 Effects of Age on Fasted Values of Cmax, AUC(last), and AUC(inf)

First, Pearson and Spearman correlations between age and each of the three PK parameters were computed. The correlation coefficients and two-sided p-values from the test of the null hypothesis of no association are shown below in TABLE VIIa:

TABLE VIIa

|  |  | ln(Cmax) | ln(AUC(last)) | ln(AUC(inf)) |
|---|---|---|---|---|
| Pearson | correlation | 0.366 | 0.289 | 0.277 |
|  | p-value | 0.017 | 0.063 | 0.076 |
| Spearman | correlation | 0.235 | 0.161 | 0.146 |
|  | p-value | 0.134 | 0.310 | 0.356 |

For all three PK parameters, the correlations are considerably larger than they were under the fed condition. In addition, the Spearman correlation coefficients, while smaller in magnitude than the Pearson correlations, are still much larger than the corresponding Spearman correlations from the fed condition. The Pearson correlation between ln(Cmax) and age is statistically significantly different from zero (p=0.017); the Pearson correlations for ln(AUC(last)) and ln(AUC(inf)) are nearly statistically significant (p=0.063 and p=0.076, respectively).

Linear regression models using the natural logarithm of each of the three, PK parameters as the dependent variable and age as the independent variable were fitted in order to estimate the magnitude of the associations with age. The estimated age effects, as well as the values of $R^2$, are displayed below in TABLE VIIb.

TABLE VIIb

|  | ln(Cmax) | ln(AUC(last)) | ln(AUC(inf)) |
|---|---|---|---|
| Regression coefficient of age | 0.0328 | 0.0268 | 0.0245 |
| $R^2$ | 0.1337 | 0.0835 | 0.0767 |

The fasted values of the regression coefficients are from 1.5 to 3 times larger than those from the fed state. In addition, the proportion of variability explained by age ranges from 7.7% for ln(AUC(inf)) to 13.4% for ln(Cmax), substantially increased over the values of $R^2$ from the fed condition.

2.5.4 Conclusions and Discussion

Under fed conditions, age has essentially no effect on ln(Cmax), ln(AUC(last)), and ln(AUC(inf)). Under fasted conditions, there is a positive association between age and each of these three PK parameters.

These results from study 101 are consistent with the results and conclusions based on the data from studies 103 and 105 (Sections 2.2-2.4). The magnitudes of the associations between the PK parameters and age are smaller, however, than those reported from studies 103 and 105. This is almost certainly due to the fact that the age range in study 101 (18-42 years) is considerably more narrow than the range of 18 to 81 years in studies 103 and 105.

The p-values from tests of statistical significance are alto less significant in study 101 than those reported in the analyses of studies 103 and 105. This is due to the fact that the magnitudes of the associations are smaller, and also to the fact that the sample size is smaller.

2.6 Effects of Age on the Fasted Values of PK Parameters Using the Data from Study 106

2.6.1 Introduction

Study 106 was a single dose trial conducted in 48 healthy volunteers. The mean age was 24.7 years, with a range from 18 to 50 years. The single treatment condition in this study was 2×400 mg without food. Blood samples for PK analyses were obtained at the same time points as in the 103 and 105 studies.

Although it is not possible to use the results of this study to confirm the results of the analyses under the fed condition, it is possible to investigate the effects of subject age on the fasted values of the PK parameters in order to determine if the effects are of similar magnitude and direction to those found in the 103 and 105 studies.

2.6.2 Effects of Age on Fasted Values of Cmax, AUC(last), and AUC(inf)

First, Pearson and Spearman correlation coefficients between age and each of the three PK parameters were computed. The correlation coefficients and two-sided p-values from the test of the null hypothesis of no association are shown below in TABLE VIIIa:

TABLE VIIIa

|  |  | ln(Cmax) | ln(AUC(last)) | ln(AUC(inf)) |
|---|---|---|---|---|
| Pearson | correlation | 0.260 | 0.349 | 0.348 |
|  | p-value | 0.074 | 0.015 | 0.016 |
| Spearman | correlation | 0.125 | 0.189 | 0.173 |
|  | p-value | 0.396 | 0.199 | 0.239 |

For ln(AUC(last)) and ln(AUC(inf)), the Pearson correlation coefficients are statistically significantly different from zero. For ln(Cmax), the Pearson correlation coefficient is nearly statistically significant. For all three variables, the nonparametric Spearman correlation coefficients are smaller than the corresponding Pearson correlation coefficients. This is not unexpected; given that the Spearman correlation coefficient is computed using only the ranks of the observations, not their actual values.

Linear regression models using the natural logarithm of each of the three PK parameters as the dependent variable and age as the independent variable were fitted in order to estimate the magnitude of the associations with age. The estimated age effects, as well as the values of $R^2$, are displayed below in TABLE VIIIb.

TABLE VIIIb

|  | ln(Cmax) | ln(AUC(last)) | ln(AUC(inf)) |
|---|---|---|---|
| Regression coefficient of age | 0.0180 | 0.0227 | 0.0230 |
| $R^2$ | 0.0676 | 0.1220 | 0.1209 |

The estimated regression coefficients are comparable to (and are actually even somewhat larger than) those reported under the fasted condition using the data from the 103 and 105 studies (Section 2.3). The relationship between ln(AUC(last)) and age and between ln(AUC(inf)) and age is statistically significant (p=0.015 and p=0.016, respectively). The relationship between ln(Cmax) and age is nearly significant (p=0.074).

2.6.3 Conclusions and Discussion

Under fasted conditions, there is a positive association between age and each of these three PK parameters. The association is significant for the two AUC parameters and nearly significant for ln(Cmax).

These results from study 106 are consistent with the results based on the fasted data from studies 103 and 105 (Sections 2.3-2.4). They are also consistent with the fasted results from study 101 (Section 2.5).

3. Effects of Age and Gender on Cmax. AUC(last), and AUC(inf)

3.1 Introduction

Section 2 investigated the effects of age on the Cmax, AUC(last), and AUC(inf) of metaxalone under fed and fasted conditions. This section extends the results of Section 2 by analyzing the joint effects of age and gender on metaxalone PK parameters under fed and fasted conditions.

Using the 2×400 mg data from studies 103 and 105, Section 3.2 presents the results of analyses of the effects of age and gender on the fed values of Cmax, AUC(last), and AUC (inf). Section 3.3 similarly reports the results of analyses of fasted values of these parameters using the 2×400 mg data from these two studies. Section 3.4 repeats the analyses of Sections 3.2 and 3.3 using the data from the 1×800 mg treatment of study 103, in combination with the 2×400 mg data from study 105. Finally, Sections 3.5 and 3.6 report the results of similar analyses using the data from studies 101 and 406, respectively.

The primary results are based on the results of linear regression models investigating the joint effects of age, gender, and the interaction between age and gender. Descriptive analyses reporting parametric (Pearson) and nonparametric (Spearman) correlation coefficients between age and each PK parameter, separately for Males and females, are also provided.

3.2 Effects of Age and Gender on Fed Values of PK Parameters Using the 2×400 mg Data from Studio 103 and 105

In study 103, 59 subjects (37 males, 22 females) were administered the 2×400 mg dose under fed conditions. The mean age was 26.1 years, with a range from 18 to 50 years. In study 105, 44 subjects (24 males, 20 females) were administered the 2×400 mg dose under fed conditions. The mean age in study 105 was 56.0 years, with a range from 48 to 81 years.

First, Pearson and Spearman correlation coefficients between age and each of the three PK parameters were computed separately in the combined group of 61 males and in the combined group of 42 females. The correlation coefficients and two-sided p-values from the test of the null hypothesis of no association are shown below in TABLE IXa:

TABLE IXa

|  |  | ln(Cmax) | ln(AUC(last)) | ln(AUC(inf)) |
|---|---|---|---|---|
| Males: |  |  |  |  |
| Pearson | correlation | −0.192 | −0.009 | −0.007 |
|  | p-value | 0.138 | 0.943 | 0.960 |

TABLE IXa-continued

|  |  | ln(Cmax) | ln(AUC(last)) | ln(AUC(inf)) |
|---|---|---|---|---|
| Spearman | correlation | −0.057 | 0.160 | 0.153 |
|  | p-value | 0.662 | 0.217 | 0.239 |
| Females: |  |  |  |  |
| Pearson | correlation | 0.189 | 0.352 | 0.381 |
|  | p-value | 0.230 | 0.022 | 0.013 |
| Spearman | correlation | 0.168 | 0.316 | 0.342 |
|  | p-value | 0.287 | 0.042 | 0.027 |

In males, all correlation coefficients are small in absolute value and are not statistically significantly different from zero. In females, there are statistically significant positive associations between ln(AUC(last)) and age and between ln(AUC(inf)) and age.

In order to investigate the joint effects of age and gender, linear regression models using the natural logarithm of each of the three PK parameters as the dependent variable were fitted. The first model considered for each of the three PK parameters included gender, age in males, and age in females as the independent variables. The purpose of this model was to test if the age effects differed between males and females. For ln(Cmax), the interaction between age and gender was nearly significant (p=0.07). However, the age effect in males was small, negative, and not statistically significantly different from zero (parameter estimate: −0.006, p-value: 0.11) and the effect in females was small, positive, and also not statistically significantly different from zero (parameter estimate: 0.004, p-value: 0.30). For ln(AUC(last)) and ln(AUC(inf)), the interaction between age and gender was not statistically significant (p=0.134 and p=0.113, respectively).

As a result, the next models included main effects for gender and age. The parameter estimates, standard errors, and p-values for the gender and age effects are shown below in TABLE IXb:

TABLE IXb

| Parameter | Statistic | ln(Cmax) | ln(AUC(last)) | ln(AUC(inf)) |
|---|---|---|---|---|
| Gender | Estimate | 0.341 | 0.394 | 0.396 |
|  | S.E. | 0.110 | 0.082 | 0.081 |
|  | p-value | 0.003 | <0.001 | <0.001 |
| Age | Estimate | −0.002 | 0.002 | 0.002 |
|  | S.E. | 0.003 | 0.002 | 0.002 |
|  | p-value | 0.536 | 0.276 | 0.236 |

For all three variables, the effect of gender is highly significant. The gender effect was parameterized as an incremental effect for females (1 for females, 0 for males). Thus, the results show that the expected values of all three variables are significantly increased in females. These results agree with the conclusions concerning the effects of gender from the clinical study report of study 106.

In comparison, the age effects are small and not statistically significantly different from zero for all three PK parameters.

As in Section 2.2, the magnitudes of the estimated effects of age under fed conditions can be more easily illustrated by considering the percentage increases when comparing a 70-year-old individual to a 20-year-old individual. On the natural log scale, the increases for ln(Cmax), ln(AUC(last)), and ln(AUC(inf)) are −1%, 1%, and 1%, respectively, for both males and females. On the untransformed scale, the corresponding differences are −8%, 12%, and 12%, respectively.

3.3 Effects of Age and Gender on Fasted Values of PK Parameters Using the 2×400 mg Data from Studies 103 and 105

In study 103, the same 59 subjects were administered the 2×400 mg dose under fasted conditions. Similarly, the 44 subjects from study 105 were administered the 2×400 mg dose under fasted conditions.

First, Pearson and Spearman correlation coefficients between age and each of the three PK parameter were computed separately in the combined group of 61 males and in the combined group of 42 females. The correlation coefficients and two-sided p-values from the test of the null hypothesis of no association are shown below in TABLE Xa.

TABLE Xa

|  |  | ln(Cmax) | ln(AUC(last)) | ln(AUC(inf)) |
|---|---|---|---|---|
| Males: |  |  |  |  |
| Pearson | correlation | 0.501 | 0.415 | 0.407 |
|  | p-value | <0.001 | <0.001 | 0.001 |
| Spearman | correlation | 0.475 | 0.477 | 0.470 |
|  | p-value | <0.001 | <0.001 | 0.001 |
| Females: |  |  |  |  |
| Pearson | correlation | 0.490 | 0.601 | 0.603 |
|  | p-value | 0.001 | <0.001 | <0.001 |
| Spearman | correlation | 0.511 | 0.621 | 0.635 |
|  | p-value | <0.001 | <0.001 | <0.001 |

In both genders, all correlation coefficients are positive and highly statistically significantly different from zero. In Section 3.2, the Pearson correlation coefficients for females in the fed condition were also statistically, significantly different from zero. However, the Pearson correlation coefficients for females in the fasted condition range in magnitude from 0.49 to 0.60 and are approximately twice as large as the corresponding Pearson correlation coefficients from the fed condition, where the corresponding range is from 0.19 to 0.38 (see Section 3.2). Thus, the extent of the association between age and PK parameters for females is greater in the fasted condition than in the fed condition.

In order to investigate the joint effects of age and gender, linear regression models using the natural logarithm of each of the three PK parameters as the dependent variable were fitted. The first model considered for each of the three PK parameters included gender, age in males, and age in females as the independent variables. The purpose of this model was to test if the age effects differed between males and females. For each of the three PK parameters, there was no evidence of significant interaction between age and gender. The p-values ranged from 0.47 to 0.72.

As a result, the next models included main effects for gender and age. The parameter estimates, standard errors, and p-values for the gender and age effects are shown below in TABLE Xb:

TABLE Xb

| Parameter | Statistic | ln(Cmax) | ln(AUC(last)) | ln(AUC(inf)) |
|---|---|---|---|---|
| Gender | Estimate | 0.368 | 0.404 | 0.405 |
|  | S.E. | 0.088 | 0.088 | 0.086 |
|  | p-value | <0.001 | <0.001 | <0.001 |
| Age | Estimate | 0.013 | 0.011 | 0.011 |
|  | S.E. | 0.002 | 0.002 | 0.002 |
|  | p-value | <0.001 | <0.001 | <0.001 |

For all three variables, the effects of both gender and age are highly significant. All parameter estimates are positive, indicating that each of the three PK parameters increases with age and are significantly increased in females in comparison to males.

The gender effects are similar in magnitude to those from the fed condition (Section 3.2). These results also agree with the conclusions concerning the effects of gender from the clinical study report of study 106. The results for age agree with those from Section 2.3.

As in Section 2.3, the magnitudes of the estimated effects of age under fasted conditions can be more easily illustrated by considering the percentage increases when comparing a 70-year-old individual to a 20-year-old individual. On the natural log scale, the increases for ln(Cmax), ln(AUC(last)), and ln(AUC(inf)) are 8%, 6%, and 6%, respectively, for both males and females. These effects are much larger than the corresponding percentage changes on the natural log scale from the fed state (Section 3.2). On the untransformed scale, the corresponding percentage increases from age 20 to age 70 in the fasted state for males and females are 84%, 78%, and 74% for Cmax, AUC(last), and AUC(inf), respectively. Again these differences are much larger than the corresponding percentage differences from the fed state (Section 3.2).

3.4 Effects of Age and Gender on Fed and Fasted Values of PK Parameters Using the 1×800 mg Data from Study 103 and the 2×400 Data from Study 105

It is possible to somewhat independently assess the consistency of the results from Sections 3.2 and 3.3 by repeating the analyses using the 1×800 fed and fasted results from study 103. These analyses are still based on the combined group of n=103 subjects (59 from study 103, 44 from study 105). However, the fed and fasted PK values from the 1×800 dosage of study 103 are used instead of the data from the 2×400 dosage.

The correlation coefficients under fed and fasted conditions for the combined group of 61 males and for the combined group of 42 females are displayed below in TABLE XIa:

TABLE XIa

|  |  | ln(Cmax) | ln(AUC(last)) | ln(AUC(inf)) |
|---|---|---|---|---|
| Fed | | | | |
| Males: | | | | |
| Pearson | correlation | −0.170 | 0.022 | 0.023 |
|  | p-value | 0.190 | 0.867 | 0.860 |
| Spearman | correlation | −0.001 | 0.188 | 0.187 |
|  | p-value | 0.996 | 0.146 | 0.149 |
| Females: | | | | |
| Pearson | correlation | 0.258 | 0.408 | 0.436 |
|  | p-value | 0.099 | 0.007 | 0.004 |
| Spearman | correlation | 0.202 | 0.410 | 0.432 |
|  | p-value | 0.199 | 0.007 | 0.004 |
| Fasted | | | | |
| Males: | | | | |
| Pearson | correlation | 0.567 | 0.447 | 0.441 |
|  | p-value | <0.001 | <0.001 | <0.001 |
| Spearman | correlation | 0.599 | 0.501 | 0.499 |
|  | p-value | <0.001 | <0.001 | 0.001 |
| Females: | | | | |
| Pearson | correlation | 0.607 | 0.596 | 0.582 |
|  | p-value | 0.001 | <0.001 | <0.001 |
| Spearman | correlation | 0.638 | 0.601 | 0.596 |
|  | p-value | <0.001 | <0.001 | <0.001 |

The estimated correlation coefficients and p-values are similar to those shown in Sections 3.2 and 3.3.

The same regression modeling strategy as was described in Sections 3.2 and 3.3 was also used. In both the fed and fasted condition, the initial models including separate age effects for males and females indicated that it was appropriate to use models with main effects for age and gender. The parameter estimates, standard errors, and p-values for the gender and age effects are shown below for the fed and fasted conditions in TABLE XIb:

| Parameter | Statistic | ln(Cmax) | ln(AUC(last)) | ln(AUC(inf)) |
|---|---|---|---|---|
| Fed | | | | |
| Gender | Estimate | 0.282 | 0.359 | 0.361 |
|  | S.E. | 0.116 | 0.085 | 0.083 |
|  | p-value | 0.017 | <0.001 | <0.001 |
| Age | Estimate | −0.000 | 0.003 | 0.003 |
|  | S.E. | 0.003 | 0.002 | 0.002 |
|  | p-value | 0.882 | 0.130 | 0.109 |
| Fasted | | | | |
| Gender | Estimate | 0.406 | 0.437 | 0.449 |
|  | S.E. | 0.098 | 0.091 | 0.090 |
|  | p-value | <0.001 | <0.001 | <0.001 |
| Age | Estimate | 0.017 | 0.012 | 0.012 |
|  | S.E. | 0.002 | 0.002 | 0.002 |
|  | p-value | <0.001 | <0.001 | <0.001 |

In both the fed and fasted conditions, there are highly significant gender effects for all three PK parameters. The age effects are not significant in the fed condition and are highly significant in the fasted condition. These results are similar to those from Sections 3.2 and 3.3. While not a completely independent confirmation (due to the fact that the 105 data are used in both analyses), these results indicate that the findings of Sections 3.2 and 3.3 are relatively robust.

3.5 Effects of Age and Gender on Fed and Fasted Values of PK Parameters Using the 1×400 mg Data from Study 101

3.5.1 Introduction

Study 101 was a two-period randomized crossover trial conducted in 42 healthy volunteers (31 males, 11 females). The mean age was 23.8 years, with a range from 18 to 42 years. The treatment conditions were 1×400 mg with food and 1×400 mg without food. Because the treatments were not the same as in the 103 and 105 studies, and additionally because the blood sample collection schedules were not the same, it is not possible to combine the 101 data with the data from studies 103 and 105. However, it is reasonable to independently investigate the effects of age and gender on the fed and fasted values of the PK parameters in order to determine if the effects are of similar magnitude and direction to those found in the 103 and 105 studies.

3.5.2 Effects of Age and Gender on Fed Values of Cmax, AUC(last), and AUC(inf)

The correlation coefficients under fed conditions for the subgroup of 31 males and separately for the subgroup of 11 females are displayed below in TABLE XIIa:

TABLE XIIa

|  |  | ln(Cmax) | ln(AUC(last)) | ln(AUC(inf)) |
|---|---|---|---|---|
| Males: | | | | |
| Pearson | correlation | 0.234 | 0.271 | 0.268 |
|  | p-value | 0.206 | 0.141 | 0.145 |
| Spearman | correlation | 0.169 | 0.094 | 0.088 |
|  | p-value | 0.363 | 0.616 | 0.637 |

TABLE XIIa-continued

|  |  | ln(Cmax) | ln(AUC(last)) | ln(AUC(inf)) |
|---|---|---|---|---|
| Females: |  |  |  |  |
| Pearson | correlation | −0.396 | −0.188 | −0.165 |
|  | p-value | 0.228 | 0.580 | 0.627 |
| Spearman | correlation | −0.645 | −0.295 | −0.244 |
|  | p-value | 0.032 | 0.379 | 0.469 |

There are no statistically significant correlation coefficients under the fed condition. The directions of the associations are positive for males and negative for females.

The same regression modeling strategy as was described in Sections 3.2 and 3.3 was also applied. The initial regression models with a gender effect and separate age effects for males and females yielded positive estimates of the age effect for males and negative estimates for females. This was consistent across all three PK parameters. However, none of the age effects was statistically significant and, in addition, there was no significant evidence of interaction between age and gender (all p-values exceeded 0.10).

As a result, the next models included main effects for age and gender. The parameter estimates, standard errors, and p-values for the gender and age effects are shown below in TABLE XIIb:

TABLE XIIb

| Parameter | Statistic | ln(Cmax) | ln(AUC(last)) | ln(AUC(inf)) |
|---|---|---|---|---|
| Gender | Estimate | 0.447 | 0.460 | 0.472 |
|  | S.E. | 0.194 | 0.159 | 0.156 |
|  | p-value | 0.027 | 0.006 | 0.004 |
| Age | Estimate | 0.007 | 0.012 | 0.012 |
|  | S.E. | 0.015 | 0.012 | 0.012 |
|  | p-value | 0.650 | 0.340 | 0.316 |

There are highly significant gender effects for all three PK parameters; the results show that the values of these parameters tend to be larger in females than in males. The estimated age effects are small and not statistically significantly different from zero.

3.5.3 Effects of Age and Gender on Fasted Values of Cmax, AUC(last), and AUC(inf)

The correlation coefficients under fasted conditions for the subgroup of 31 males and separately for the subgroup of 11 females are displayed below in TABLE XIIIa:

TABLE XIIIa

|  |  | ln(Cmax) | ln(AUC(last)) | ln(AUC(inf)) |
|---|---|---|---|---|
| Males: |  |  |  |  |
| Pearson | correlation | 0.384 | 0.279 | 0.287 |
|  | p-value | 0.344 | 0.406 | 0.390 |
| Spearman | correlation | 0.206 | 0.127 | 0.115 |
|  | p-value | 0.267 | 0.495 | 0.539 |
| Females: |  |  |  |  |
| Pearson | correlation | 0.309 | 0.284 | 0.208 |
|  | p-value | 0.356 | 0.398 | 0.538 |
| Spearman | correlation | 0.525 | 0.406 | 0.235 |
|  | p-value | 0.097 | 0.216 | 0.487 |

All correlation coefficients are positive for both males and females. However, only the Pearson correlation between ln(Cmax) and age in males is statistically significantly different from zero.

The same regression modeling strategy as was described in Sections 3.2 and 3.3 was also applied. The initial regression models with a gender effect and separate age effects for males and females yielded positive estimates of the age effect for both males and females and there was no significant evidence of interaction (all p-values exceeded 0.60) for males and negative estimates for females.

As a result, the next models included main effects for age and gender. The parameter estimates, standard errors, and p-values for the gender and age effects are shown below in TABLE XIIIb:

TABLE XIIIb

| Parameter | Statistic | ln(Cmax) | ln(AUC(last)) | ln(AUC(inf)) |
|---|---|---|---|---|
| Gender | Estimate | 0.452 | 0.465 | 0.500 |
|  | S.E. | 0.156 | 0.167 | 0.156 |
|  | p-value | 0.006 | 0.008 | 0.003 |
| Age | Estimate | 0.029 | 0.023 | 0.021 |
|  | S.E. | 0.012 | 0.013 | 0.012 |
|  | p-value | 0.021 | 0.082 | 0.097 |

There are highly significant gender effects for all three PK parameters. The results show that the values of these three PK parameters tend to be larger in females than in males. The estimated age effects are much larger in the fasted condition than in the fed condition (Section 3.5.2). The effect of age to the fasted condition is statistically significant for ln(Cmax) and nearly significant for ln(AUC(last)) and ln(AUC(inf)). These results confirm those from Sections 3.2 and 3.6 Effects of Age and Gender on Fasted Values of PK Parameters Using the 2×400 mg Data from Study 106

Study 106 was a single dose trial conducted in 48 healthy volunteers (24 males, 24 females). The mean age was 24.7 years, with a range from 18 to 50 years. The single treatment condition in this study was 2×400 mg without food. Blood samples for PK analyses were obtained at the same time points as in the 103 and 105 studies.

Although this study, did not provide any data under fed conditions, it is possible to investigate the effects of subject age and gender on the fasted values of the PK parameters in order to determine if the effects are of similar magnitude and direction to those found in the 103 and 105 studies.

The correlation coefficients under fasted conditions for the subgroup of 24 males and separately for the subgroup of 24 females are displayed below in TABLE XIVa:

TABLE XIVa

|  |  | ln(Cmax) | ln(AUC(last)) | ln(AUC(inf)) |
|---|---|---|---|---|
| Males: |  |  |  |  |
| Pearson | correlation | −0.202 | −0.178 | −0.184 |
|  | p-value | 0.344 | 0.406 | 0.390 |
| Spearman | correlation | −0.316 | −0.365 | −0.368 |
|  | p-value | 0.132 | 0.079 | 0.077 |
| Females: |  |  |  |  |
| Pearson | correlation | 0.336 | 0.431 | 0.416 |
|  | p-value | 0.108 | 0.035 | 0.043 |
| Spearman | correlation | 0.279 | 0.428 | 0.368 |
|  | p-value | 0.187 | 0.037 | 0.076 |

The signs of the correlation coefficients are negative for males and positive for females. The only correlation coefficients that are statistically significantly different from zero are those between age and ln(AUC(last)) and between age and ln(AUC(inf)) for females. Note, however, that the corresponding Spearman correlation coefficient between age and ln(AUC(inf)) for females is not statistically significantly different from zero.

The same regression modeling strategy as was described in Sections 3.2 and 3.3 was also used. In the initial regression models with a gender effect and separate age effects for males and females, the parameter estimates for all three variables were negative for males and positive for females. In addition, the age effect in females was statistically significant for ln(AUC(last)) and ln(AUC(inf)). However, the tests of equality between the age effects for males and females (i.e., the age-by-gender interaction) were not statistically significant for any of the three variables; the p-values ranged from 0.08 to 0.11.

As a result, the next models included main effects for age and gender. The parameter estimates, standard errors, and p-values for the gender and age effects are shown below in TABLE XIVb:

TABLE XIVb

| Parameter | Statistic | ln(Cmax) | ln(AUC(last)) | ln(AUC(inf)) |
|---|---|---|---|---|
| Gender | Estimate | 0.414 | 0.406 | 0.424 |
| | S.E. | 0.169 | 0.152 | 0.154 |
| | p-value | 0.018 | 0.010 | 0.008 |
| Age | Estimate | 0.010 | 0.014 | 0.014 |
| | S.E. | 0.010 | 0.009 | 0.009 |
| | p-value | 0.342 | 0.115 | 0.122 |

The gender effects are of the same magnitude and direction as in the corresponding models for the fasted condition from Sections 3.3-3.5. The gender effect is statistically significant for all three PK parameters. The age effects are positive for all three variables, indicating that increasing age is associated with higher values of the PK parameters. However, none of the age effects is statistically significant in study 106.

4. Conclusions

Using the data from four studies (101, 103, 105, 106), the effects of age, as well as the joint effects of age and gender, on ln(Cmax), ln(AUC(last)), and ln(AUC(inf)) under fed and fasted conditions were investigated. The results of the various analyses are remarkably similar, and can be summarized as follows:

Ignoring gender, age has essentially no effect on ln(Cmax) under fed conditions; and little effect on ln(AUC(last)), and ln(AUC(inf)).

Ignoring gender, there is a strong and consistent association age and each of the three PK parameters under fasted conditions. As age increases, the values of the fasted PK parameters tend to increase.

Gender has a statistically significant effect on metaxalone PK parameters under both fed and fasted conditions. This result is uniformly consistent across all studies and all analyses. Females tend to have larger values of Cmax, AUC(last), and AUC(inf) than males.

In the models that include the effect of gender; age has little or no effect on metaxalone PK parameters under Ted conditions. Although the direction of the association tends to be positive (as is also the case when not adjusting for the effects of gender), there are no instances of statistically significant associations between age and PK parameters under fed conditions.

In the models that include the effect of gender, there is a positive association between age and each of the three PK parameters under fasted conditions. As age increases, the values of the fasted PK parameters tend to increase.

Thus, the overall conclusion is that variations in the population, due to age, in the bioavailability of metaxalone are minimized when metaxalone is taken in the fed state. Given the magnitude of the plasma level changes of metaxalone seen in the fasted state as age increases, metaxalone should be administered with food. And in order to ensure more consistent levels of metaxalone, it is recommended that the drug be administered with food.

Article of Manufacture

The article of manufacture comprises a container holding an immediate release pharmaceutical composition suitable for oral administration of metaxalone in combination with printed labeling instructions providing a discussion of when a particular dosage form should be administered with food and when it should be taken on an empty stomach. The composition will be contained in any suitable container capable of holding and dispensing the dosage form and which will not significantly interact with the composition.

The labeling may advise that administration of metaxalone with food increases bioavailability and may advise that administration of metaxalone with food reduces the effect of age on bioavailability, or reduces the age-related variability in bioavailability. The labeling may advise that metaxalone should be taken with food, for the desired effect of increasing bioavailability, or for the desired effect of reducing the effect of age on bioavailability, or reducing the age-related variability in bioavailability. The labeling may advise that metaxalone should be administered with food, given the magnitude of the plasma level changes of metaxalone seen in the fasted state as age increases. Alternatively, or additionally, the labeling may recommend that the drug be administered with food in order to ensure more consistent levels of metaxalone.

The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

While the invention has been described by discussion of embodiments of the invention and non-limiting examples thereof, one of ordinary skill in the art may, upon reading the specification and claims, envision other embodiments and variations which are also within the intended scope of the invention and therefore the scope of the invention shall only be construed and defined by the scope of the appended claims.

What is claimed is:

1. A method of reducing the effect of a patient's age on the oral bioavailability of metaxalone in a patient receiving metaxalone therapy comprising administering to the patient a therapeutically effective amount of metaxalone in a pharmaceutical composition with food over the course of said therapy.

2. The method of claim 1, wherein the therapeutically effective amount is 200 mg to 900 mg.

3. The method of claim 1, wherein the therapeutically effective amount is 400 mg to 800 mg.

4. The method of claim 1, wherein the administration to the patient occurs between 30 minutes prior to 2 hours after consuming food.

5. The method of claim 1, wherein the administration to the patient is substantially at the same time as the consumption of food.

6. The method of claim 4, wherein the administration to the patient is within 15 minutes of the consumption of food.

7. The method of claim 1, wherein the pharmaceutical composition comprises a tablet.

8. The method of claim 1, wherein the tablet is in unit dosage form.

9. The method of claim 1, further comprising informing the patient that the administration of a therapeutically effective amount of metaxalone in a pharmaceutical composition with food results in a decreased effect of patient's age on bioavailability of metaxalone, compared to administration without food.

10. The method of claim 1, wherein the metaxalone is from a container with printed labeling advising that administration of a therapeutically effective amount of metaxalone in a pharmaceutical composition with food results in a decreased effect of patient's age on bioavailability of metaxalone, compared to administration without food.

11. A method of using metaxalone in the treatment of musculoskeletal conditions comprising:
administering to a patient with a therapeutically effective amount of metaxalone; and
informing the patient that the administration of metaxalone with food results in a decrease in the effect of patient's age on at least one of C(max), AUC(last), and AUC(inf) of metaxalone compared to administration without food.

12. The method according to claim 11, wherein the therapeutically effective amount of metaxalone comprises 200 mg to 900 mg of metaxalone.

13. The method according to claim 12, wherein the therapeutically effective amount of metaxalone comprises 400 mg to 800 mg of metaxalone.

14. The method according to claim 11, wherein the metaxalone is provided in tablet form.

15. The method according to claim 14, wherein the tablet is in unit dosage form.

16. A method of using metaxalone in the treatment of musculoskeletal conditions comprising:
informing a patient with musculoskeletal conditions that the administration of a therapeutically effective amount of metaxalone with food results in a decrease in the effect of patient's age on at least one of C(max), AUC (last), and AUC(inf) of metaxalone compared to administration without food,
wherein the patient administers the metaxalone in accordance with the information provided.

17. A method of using metaxalone in the treatment of musculoskeletal conditions comprising:
obtaining the metaxalone from a container providing information that the administration of metaxalone with food decreases the effect of patient's age on at least one of C(max), AUC(last), and AUC(inf) of metaxalone compared to administration without food, and
ingesting the metaxalone with food.

18. A method of using metaxalone in the treatment of musculoskeletal conditions comprising:
administering to a patient in need of treatment a therapeutically effective amount of metaxalone, with food; and
informing the patient that the administration of a therapeutically effective amount of metaxalone in a pharmaceutical composition with food results in a decrease in the effect of patient's age on at least one of C(max), AUC (last), and AUC(inf) of metaxalone, as compared to administration of metaxalone in a fasted state;
wherein the administration of metaxalone with food results in a decrease in the effect of patient's age on at least one of C(max), AUC(last), and AUC(inf) of metaxalone, as compared to administration of metaxalone in a fasted state.

19. The method according to claim 18, wherein the metaxalone is from a container with printed labeling advising that administration with food results in a decrease in the effect of patient's age on at least one of C(max), AUC(last), and AUC (inf) of metaxalone, as compared to administration of metaxalone in a fasted state.

20. The method according to claim 18, wherein the metaxalone is provided in tablet form.

21. The method according to claim 20, wherein the metaxalone is provided in 400 mg tablet form.

22. The method according to claim 18, wherein the printed labeling further advises that administration of the metaxalone with food results in an increase in the C(max) of 177.5%.

23. The method according to claim 18, wherein the printed labeling further advises that administration of the metaxalone with food results in an increase in the AUC(last) of 123.5%.

24. The method according to claim 18, wherein the printed labeling further advises that administration of the metaxalone with food results in an increase in AUC(inf) of 115.4%.

25. The method according to claim 18, wherein the metaxalone is provided in 400 mg tablet form, and the printed labeling further advises that administration of metaxalone with food results in an increase in the C(max), AUC(last), and AUC(inf), of 177.5%, 123.5%, and 115.4%, respectively, compared to administration of metaxalone in a fasted state.

26. A method of achieving consistent plasma levels of metaxalone in any given patient regardless of patient's age comprising administering to a patient a therapeutically effective amount of metaxalone with food, wherein said administration achieves consistent levels of metaxalone in any given patient regardless of patient's age.

27. A method of reducing variations in metaxalone bioavailability comprising administering to a patient with food a therapeutically effective amount of metaxalone in a pharmaceutical composition, wherein said administration reduces variations in metaxalone bioavailability.

* * * * *

UNITED STATES PATENT AND TRADEMARK OFFICE
CERTIFICATE OF CORRECTION

| | | |
|---|---|---|
| PATENT NO. | : 7,714,006 B1 | Page 1 of 1 |
| APPLICATION NO. | : 11/182661 | |
| DATED | : May 11, 2010 | |
| INVENTOR(S) | : Michael C. Scaife et al. | |

It is certified that error appears in the above-identified patent and that said Letters Patent is hereby corrected as shown below:

On the Title page, Item (75), the second inventor's name "Charles C. Davis" should read --Charles S. Davis--.

Col. 2, line 19, "ht" should read --in--.

Col. 5, line 45, col. 7, line 17, Table IIIa, Table IIIb, Table IVa, Table IVb, Table Va, Table Vb, Table VIa, Table VIb, Table VIIa, Table VIIb, Table VIIIa, Table VIIIb, Table IXa, Table IXb, Table Xa, Table Xb, Table XIa, Table XIb, Table XIIa, Table XIIb, Table XIIIa, Table XIIIb, Table XIVa, and Table XIVb, each of "In" should read --ln--.

Col. 9, line 51, "AU" should read --All--.

Col. 10, line 35, "ma" should read --mg--.

Col. 13, line 9, "alto" should read --also--.

Col. 14, line 36, "406" should read --106--.

Col. 14, line 46, "Studio" should read --Studies--.

Col. 14, line 52, "48" should read --18--.

Col. 20, line 27, "to" should read --in--.

Col. 21, line 46, insert --between-- before "age".

Col. 21, line 57, "Ted" should read --fed--.

Signed and Sealed this

Twenty-fourth Day of August, 2010

David J. Kappos
*Director of the United States Patent and Trademark Office*